United States Patent [19]
Enders et al.

[11] 3,975,534
[45] Aug. 17, 1976

[54] PHARMACEUTICAL COMPOSITIONS USEFUL FOR TREATING TICK INFESTATION IN ANIMALS WHICH CONTAIN 2-ARYLIMINOPYRROLIDINES OR THEIR SALTS AS THE ACTIVE AGENT

[75] Inventors: Edgar Enders, Cologne; Wilhelm Stendel, Wuppertal-Elberfeld; Jurgen-Dietrich Meier, Cologne; Marc Francque, Monheim, all of Germany

[73] Assignee: Bayer Aktiengesellschaft, Germany

[22] Filed: Jan. 24, 1974

[21] Appl. No.: 436,090

Related U.S. Application Data

[62] Division of Ser. No. 181,613, Sept. 17, 1971, Pat. No. 3,821,204.

[30] Foreign Application Priority Data
Sept. 19, 1970 Germany............................ 2046413

[52] U.S. Cl. ............................. 424/274; 260/240 F
[51] Int. Cl.² ........................................ A61K 31/40
[58] Field of Search................ 260/326.85; 424/274

[56] References Cited
UNITED STATES PATENTS
3,821,204  6/1974  Enders et al. .................. 260/240 F FOREIGN PATENTS OR APPLICATIONS
6,903,653  12/1969  South Africa.................. 260/326.85

Primary Examiner—V. D. Turner

[57] ABSTRACT

2-Phenyliminopyrrolidines of the formula:

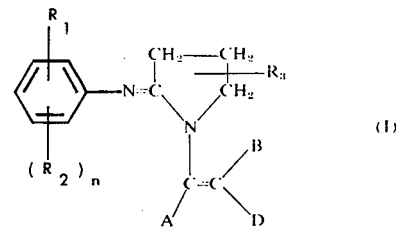

or salts thereof,
wherein
$R_1$ is halogen,
$R_2$ is hydrogen, halogen, alkyl of 1 to 6 carbon atoms, difluoromethyl or trifluoromethyl,
$R_3$ is hydrogen or alkyl, preferably lower alkyl,
$n$ is an integer from 1 to 4, and
A, B and D each represent hydrogen, alkyl of 1 to 6 carbon atoms, alkenyl of 2 to 6 carbon atoms, or A and B, or B and D are linked to each other to form a ring, provided that at least one of A, B and D is alkyl or alkenyl,
are useful as acaricides.

132 Claims, No Drawings

PHARMACEUTICAL COMPOSITIONS USEFUL FOR TREATING TICK INFESTATION IN ANIMALS WHICH CONTAIN 2-ARYLIMINOPYRROLIDINES OR THEIR SALTS AS THE ACTIVE AGENT

This is a division of application Ser. No. 181,613, filed Sept. 17, 1971, which issued as U.S. Pat. No. 3,821,204 on June 28, 1974.

The present invention relates to certain new 2-phenyliminopyrrolidines, to a process for their production, to acaricidal compositions and to their use as acaricides, especially in combating animal ectoparasites.

More particularly, the compounds of the present invention are 2-phenyliminopyrrolidines of the formula:

(I)

and salts thereof,
wherein
$R_1$ is halogen,
$R_2$ is hydrogen, halogen, alkyl of 1 to 6 carbon atoms, difluoromethyl or trifluoromethyl,
$R_3$ is hydrogen or alkyl, preferably lower alkyl,
$n$ is an integer from 1 to 4, and
A, B and D each represent hydrogen, alkyl of 1 to 6 carbon atoms, alkenyl of 2 to 6 carbon atoms, or A and B, or B and D are linked to each other to form a ring, provided that at least one of A, B and D is alkyl or alkenyl.

These compounds exhibit strong acaricidal properties and are therefore useful for combating animal ectoparasites from the class of the acarids.

The compounds according to the present invention may be produced by condensing an arylamine of the formula:

(II)

wherein
$R_1$, $R_2$ and $n$ are as above defined, with a pyrrolidone of the formula:

(III)

wherein
$R_3$, A, B and D are as above defined,
in the presence of an agent which splits off water. The compounds of the present invention may, for example, be isolated in the form of their salts with hydrohalic acids or in the form of the free bases which may then be converted into suitable salts if desired.

The condensation of 2,4-dichloroaniline and N-isobutenyl-pyrrolidone can be represented by the following equation:

(IV)

The arylamines defined by the formula (II) are known. $R_1$ is preferably chlorine, bromine or fluorine. When $R_2$ is halogen, it is preferably chlorine, bromine or fluorine; when it is alkyl, it is preferably methyl or ethyl.

Examples of arylamines of formula (II) include: 2-, 3- and 4-chloroaniline, 2-, 3- and 4-bromoaniline, 2,4-dichloroaniline, 3,4-dichloroaniline, 2,3-dichloroaniline, 2,5-dichloroaniline, 2,4,5-trichloroaniline, 2,4,6-trichloroaniline, 3,4,5-trichloroaniline, 4-fluoro-3-chloro-aniline, 4-fluoro-2-bromo-aniline, 2-chloro-4-bromo-aniline, 4-chloro-2-bromo-aniline, 2,4-dibromo-aniline, 4-bromo-2-methyl-aniline, 2,5-dichloro-4-bromo-aniline, 4,5-dichloro-2-bromo-aniline, 2-fluoro-4-bromo-aniline, 2,3,4-trichloro-aniline, 2,3,4,5-tetrachloro-aniline, pentachloroaniline, 4-chloro-2-methylaniline, 2-chloro-4-methyl-aniline, 2,4-dichloro-5-methyl-aniline, 3,4-dichloro-6-methyl-aniline, 2-chloro-4-fluoro-aniline, 4-chloro-2-ethyl-aniline 4-iodo-2-chloro-aniline, 4-bromo-2-ethylaniline, 4-bromo-2-isopropyl-aniline, 2-chloro-4-difluoromethyl-aniline, 2-chloro-4-trifluoromethyl-aniline, 4-chloro-2-difluoromethyl-aniline, 4-chloro-2-trifluoromethyl-aniline, 4-chloro-3-trifluoromethyl-aniline and 3-chloro-4-trifluoromethyl-aniline.

The pyrrolidones of formula (III) are either known or can be produced according to known methods.

$R_3$ is preferably hydrogen; when it is alkyl, it is preferably alkyl of 1 to 4 carbon atoms.

When A and B are linked to each other to form a ring, it is preferred that a 6-membered ring is formed. The preferred alkyl and alkenyl groups are those having the appropriate number of carbon atoms to form a 6-membered ring.

Examples of pyrrolidones of formula (III) include: N-propenyl-pyrrolidone, N-isopropenyl-pyrrolidone, N-butenyl-pyrrolidone, N-isobutenyl-pyrrolidone, N-pentenyl-pyrrolidone, N-hexenyl-pyrrolidone, N-(1,2-dimethyl-vinyl)-pyrrolidone, N-(1,2,2-trimethyl-vinyl)-pyrrolidone, N-(1-ethyl-2-methyl-vinyl)-pyrrolidone, N-(1-methyl-2-isopropyl-vinyl)-pyrrolidone, N-(2-isopropyl-vinyl)-pyrrolidone, N-cyclopentenyl-pyrrolidone, N-cyclohexenyl-pyrrolidone, N-(2,2-cyclo-tetramethylene-vinyl)-pyrrolidone, N-(2,2-cyclopentyl-methylene-vinyl)-pyrrolidone, 4-(N-pyrrolidonyl-methylene)-cyclohexene and 1-(N-pyrrolidonyl)-butadiene.

N-isobutenyl-pyrrolidone can, for example, be produced by reacting pyrrolidone with isobutyraldehyde under the conditions of an azeotropic distillation, in the presence of acid catalysts, or by splitting off methanol from the corresponding amidal-acetal or by splitting off hydrogen chloride from the corresponding amidal-chloride, as illustrated in the following formula scheme:

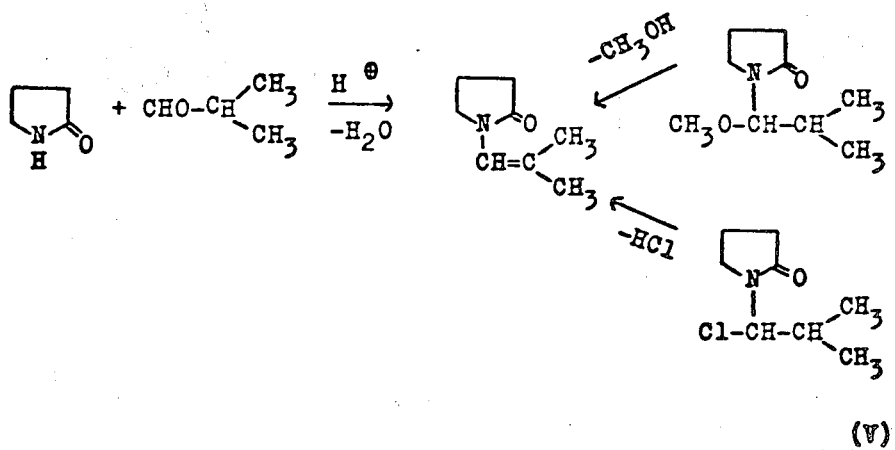

(V)

The reaction of the arylamine with the pyrrolidone derivative can be carried out in the presence of an inert diluent. Suitable diluents are organic solvents, for example aromatic hydrocarbons such as benzene, toluene and xylene, and chlorinated hydrocarbons such as chlorobenzene, O-dichlorobenzene, tetrachloromethane and tetrachloroethylene.

An inorganic acid halide, such as phosphorus oxychloride, phosphorus trichloride, thionyl chloride, phosphorus sulpho-chloride or phosgene is preferably used as the agent which splits off water.

The reaction temperatures can be varied over a wide range. In general, the reaction is carried out at 10° to 120°, preferably 60° to 100°C.

In carrying out the process, the two starting materials may be used in approximately equimolar amounts and an approximately equimolar amount of the agent which splits off water may be added. The reaction can be carried out in the presence of solvents, but preferably in the absence of any solvents. In general, all reactants are first brought together and the reaction mixture is then heated to higher temperatures, for example 60° – 100°C. The reaction is complete when the aniline derivative employed can no longer be detected by diazotisation and coupling. The 2-phenylimino-pyrrolidines may be obtained as salts of hydrohalic acids, which are sparingly soluble in hydrocarbons or halogenated hydrocarbons. They can be isolated as such salts. Preferably, however, the salts produced are dissolved in water at room temperature, preferably a large amount of water, oily, insoluble by-products are removed, and the free bases are precipitated by the addition of aqueous sodium hydroxide solution. The bases can be filtered off as crystalline precipitates, or, if they possess low solidification points, can be extracted with organic solvents, dried and distilled. To prepare any desired salts, the free bases can be reacted with the corresponding acids, for example with inorganic acids such as sulphuric acid, hydrochloric acid or phosphoric acid, or with organic acids such as acetic acid, tartaric acid, citric acid, benzenesulphonic acid and naphthalene-1,5-disulphonic acid.

To prepare the compounds according to the invention, the arylamines of the formula (II) can also be reacted with pyrrolidine derivatives of the formula (VI) or (VII);

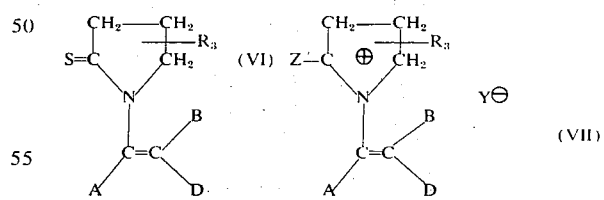

wherein
$R_3$, A, B and D are as above defined,
Z is a reactive ester or ether group and
$Y^-$ is the anion of an inorganic acid.

As examples, there may be mentioned N-isobutenyl-2-thiopyrrolidone, N-isobutenyl-2-ethoxy-pyrrolinium tetrafluoborate, N-isobutenyl-2-methylthiopyrrolinium methosulphate, N-isobutenyl-2-chloropyrrolinium chloride or acetals such as N-isobutenyl-2,2-dimethoxy-pyrrolidine.

The compounds according to the invention can furthermore be obtained by splitting off alcohol or hydrogen halide from compounds of the formula (VIII) or (IX):

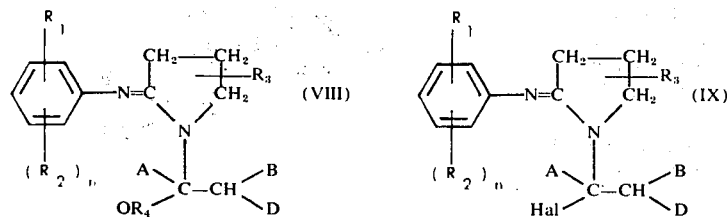

wherein
$R_1$, $R_2$, $R_3$, $n$, A, B and D are as above defined,
$R_4$ is alkyl of 1 to 6 carbon atoms, preferably methyl or ethyl, and
Hal is chlorine or bromine.

Finally, the compounds of the present invention can also be obtained by reacting pyrrolidine derivatives of the formula (X) with aldehydes or ketones of the formula (IX) while splitting off water, for example under the conditions of an azeotropic distillation in the presence of acid catalysts:

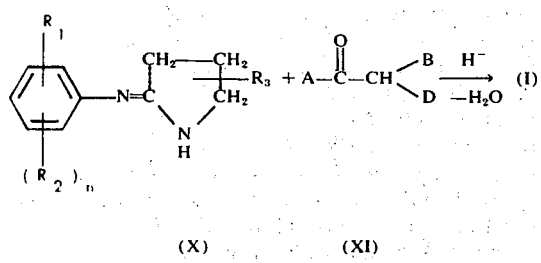

In the formulae (X) and (XI),
$R_1$, $R_2$, $R_3$, $n$, A, B and D are as above defined.

The 2-phenylimino-pyrrolidines as well as their salts display strong acaricidal properties, especially against acarids which as animal ectoparasites attack domesticated animals such as cattle, sheep and rabbits. At the same time, the pyrrolidine derivatives generally have only a low toxicity to warm-blooded animals. They are therefore well suited to combating animal ectoparasites of the class acarids.

The compounds of the present invention show a considerably better activity than similar 2-phenylimino-pyrrolidines, such as have been disclosed in Belgian Pat. No. 734,934.

As economically important, harmful ectoparasites of the class of the acarids, which play a major role especially in tropical and sub-tropical countries, there may be mentioned the Australian and the South American cattle tick, Boophilus microplus, and the South African cattle tick, Boophilus decoloratus, both from the family of the ixodidae. In the same way, representatives of the family of the sarcoptidae can also be combated, such as the rabbit ear mite, Psoroptes cuniculi.

Over the course of time, various ectoparasites, especially ticks, have become resistant to the phosphoric acid esters and carbamates hitherto used for combating them, so that in many areas the success in combating them has become increasingly doubtful. To ensure economical raising of animals in the areas where attack occurs, there is an urgent requirement for agents by means of which all stages of development, that is to say larvae, nymphs, metanymphs and adults, even of resistant strains, for example of the genus Boophilus, can be combated reliably. For example, in Australia the Ridgeland strain and the Biarra strain in Boophilus microplus are highly resistant to the phosphoric acid ester agents hitherto used [see also R. H. Wharton and W. J. Roulston, Annual Review of Entomology, volume 15 (1970), pages 381–404].

The compounds of the present invention are equally active both against the normally sensitive strains and against the resistant strains, for example of Boophilus.

On normal application to the host animal, they both have a direct lethal action on all forms existing as parasites on the animal, and a strong ovicidal action on the adult forms, so that the reproductive cycle of the ticks is interrupted both in the parasite phase on the animal and in the non-parasitic phase. The deposition of eggs is largely stopped and development and hatching inhibited.

The compounds of the present invention can be formulated into acaricidal compositions in the form of solutions, emulsions, suspensions, powders, pastes and granulates. These may be produced according to techniques per se known, for example, by mixing the active compounds with extenders, that is, liquid or solid or liquefied gaseous diluents or carriers, optionally with the use of surface-active agents, that is, emulsifying agents and/or dispersing agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions with boiling ranges of 120° – 400°C, preferably 180° – 300°C, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide, pyrrolidone, N-methyl-pyrrolidone, hexamethyl-phosphoric acid amide or acetonitrile, as well as water.

By liquefied gaseous diluents or carriers are meant liquids which would be gaseous at normal temperatures and pressures, e.g. aerosol propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying agents include nonionic and anionic emulsifiers, such as polyoxyethylene-fatty acid esters, polyoxyethylene-fatty alcohol ethers, for example alkylarylpolyglycol ethers, alkyl sulphonates, alkyl sulphates, quaternary ammonium salts with long chain alkyl moieties and aryl sulphonates; and preferred examples of dispersing agents include lignin, sulphite waste liquors and methyl cellulose.

The acaricidal compositions of the present invention contain 0.1 to 95% by weight of active substance, preferably 0.5 to 90% by weight.

For application they may be diluted, for example with water. Depending on the form of use, the concentrations can be varied over a wide range and are generally from 10 to 50,000 ppm by weight, preferably 50 to 5,000 ppm.

Application may be effected in the usual manner, for example by spraying, watering or atomizing, or in a bath (dip).

Other additives of active substances, such as disinfectants, can be mixed with the formulations of the ready-to-use solutions.

Aqueous solutions or emulsions of the compounds of the present invention possess good stability under practical conditions, so that they may remain active for up to three months or longer at a pH of 7 – 9.

The present invention also provides a method of combating acarid pests which comprises applying to the acarids or a habitat thereof a compound of the present invention per se or in the form of an acaricidal composition containing as the active ingredient a compound of the present invention in combination with a diluent or carrier.

The present invention also provides a method of protecting or freeing animals from ectoparasites which comprises applying externally to the animals a compound of the invention alone or in admixture with a diluent or carrier.

The following non-limitative examples more particularly illustrate the present invention.

EXAMPLE 1

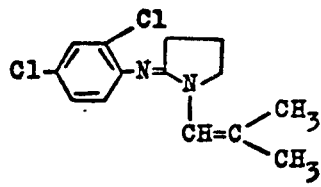

512 g of phosphorus oxychloride are added dropwise to a mixture of 500 g of N-isobutenyl-pyrrolidone and 543 g of 2,4-dichloroaniline at 15° – 20°. Thereafter the mixture is stirred for a further hour at 20° and is then heated to 80° – 85° until no further 2,4-dichloroaniline is detectable in a sample by diazotisation and coupling. Thereafter the batch is introduced into 30 liters of water at 20° – 25°C, with stirring, and the mixture is stirred for 1 hour until only small amounts of oily material still remain undissolved. After adding active charcoal and a filter aid, the acidic aqueous solution is clarified by filtration and adjusted to pH 8 – 8.5 and 20° – 30°C by dropwise addition of 45% strength sodium hydroxide solution. Thereupon the reaction product precipitates in the form of colourless to pale yellowish crystals; if necessary, the mixture is seeded with a small amount of crystalline reaction product. The suspension is stirred for a further 30 minutes and the product is filtered off and rinsed with a large amount of water. After drying in vacuo, the yield is 830 g (87.5% of theory), melting point: 50° – 52°C; after recrystallisation from petroleum ether, melting point: 54.5°C. The purity, determined by gas chromatography, is 98 – 100%. The compound can be distilled and has a boiling point at a pressure of 0.2 mm Hg of 155° – 158°C.

The 2-arylimino-1-alkylvinyl-pyrrolidines of Examples 2–34 are analogously produced from the appropriate N-alkylvinylpyrrolidone and the arylamine.

| Example No. | Formulae of Examples 2–34 | Physical constants |
|---|---|---|
| 2 | 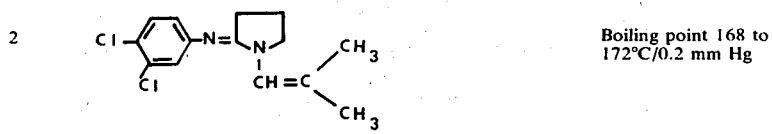 | Boiling point 168 to 172°C/0.2 mm Hg |
| 3 | 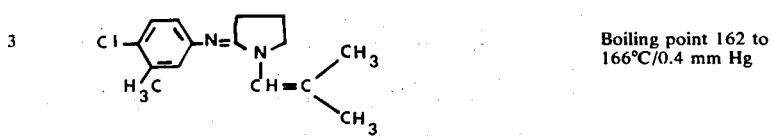 | Boiling point 162 to 166°C/0.4 mm Hg |
| 4 | 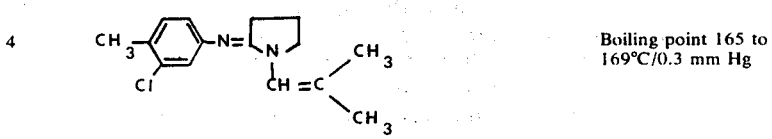 | Boiling point 165 to 169°C/0.3 mm Hg |

-continued

| Example No. | Formulae of Examples 2–34 | Physical constants |
|---|---|---|
| 5 | Br—⟨C₆H₃(CH₃)⟩—N=⟨pyrrolidine with CH=C(CH₃)₂⟩ | Boiling point 171 to 176°C/0.3 mm Hg |
| 6 | CH₃—⟨C₆H₃(Br)⟩—N=⟨pyrrolidine with CH=C(CH₃)₂⟩ | Boiling point 172 to 176°C/0.3 mm Hg |
| 7 | Br—⟨C₆H₃(C₂H₅)⟩—N=⟨pyrrolidine with CH=C(CH₃)₂⟩ | Boiling point 172 to 176°C/1.0 mm Hg |
| 8 | F₃C—⟨C₆H₃(Cl)⟩—N=⟨pyrrolidine with CH=C(CH₃)₂⟩ | Boiling point 162 to 166°C/0.3 mm Hg |
| 9 | ⟨C₆H₄(Cl)⟩—N=⟨pyrrolidine with CH=C(CH₃)₂⟩ | Boiling point 157 to 162°C/0.4 mm Hg |
| 10 | ⟨C₆H₃(Cl)(CH₃)⟩—N=⟨pyrrolidine with CH=C(CH₃)₂⟩ | Boiling point 158 to 162°C/0.3 mm Hg |
| 11 | ⟨C₆H₂(Cl)(Cl)(CH₃)⟩—N=⟨pyrrolidine with CH=C(CH₃)₂⟩ | Boiling point 172 to 176°C/0.3 mm Hg |

| Example No. | Formulae of Examples 2–34 | Physical constants |
|---|---|---|
| 12 | 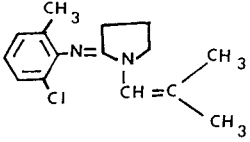 | Boiling point 139 to 143°C/0.3 mm Hg |
| 13 | 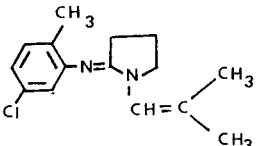 | Boiling point 151 to 156°C/0.2 mm Hg |
| 14 | 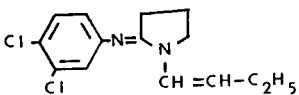 | Boiling point 162 to 165°C/0.2 mm Hg |
| 15 | 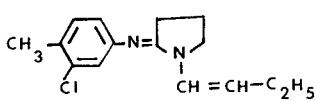 | Boiling point 157 to 163°C/0.3 mm Hg |
| 16 | 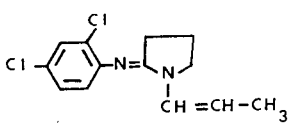 | Boiling point 140 to 143°C/0.2 mm Hg |
| 17 | 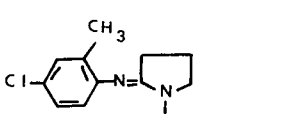 | Boiling point 139 to 142°C/0.2 mm Hg |
| 18 | 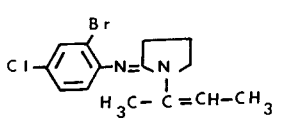 | Boiling point 167 to 171°C/0.3 mm Hg |
| 19 | 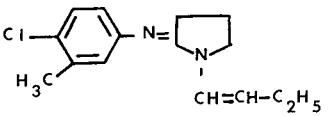 | Boiling point 158–164°/0.5 mm Hg |

-continued
| Example No. | Formulae of Examples 2–34 | Physical constants |
|---|---|---|
| 20 |  | Boiling point 152–157°/0.3 mm Hg |
| 21 | 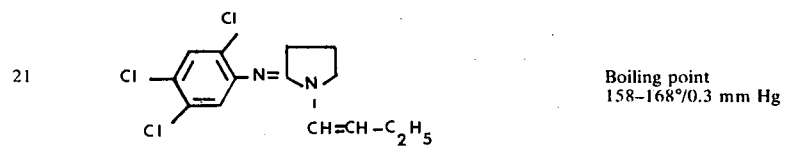 | Boiling point 158–168°/0.3 mm Hg |
| 22 | 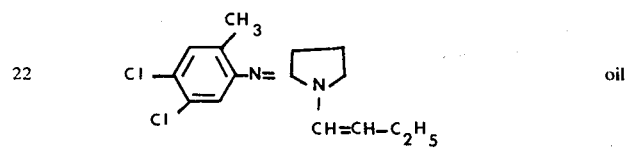 | oil |
| 23 | 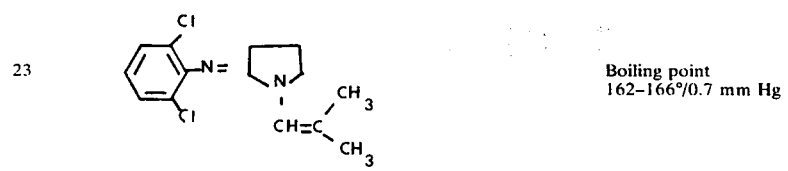 | Boiling point 162–166°/0.7 mm Hg |
| 24 | 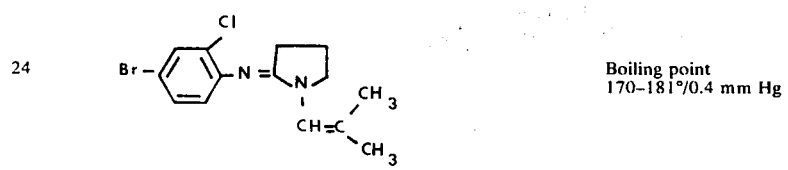 | Boiling point 170–181°/0.4 mm Hg |
| 25 | 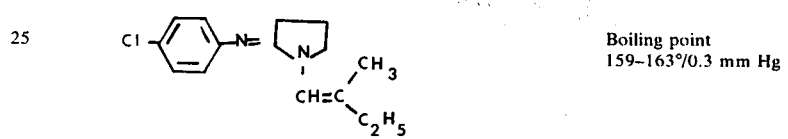 | Boiling point 159–163°/0.3 mm Hg |
| 26 | 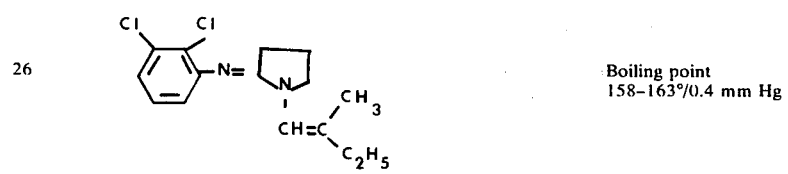 | Boiling point 158–163°/0.4 mm Hg |

| Example No. | Formulae of Examples 2–34 | Physical constants |
|---|---|---|
| 27 | 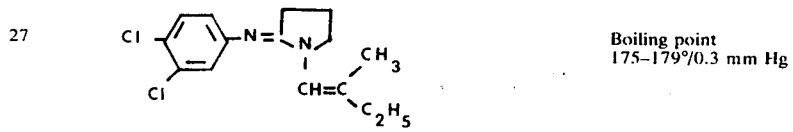 | Boiling point 175–179°/0.3 mm Hg |
| 28 | 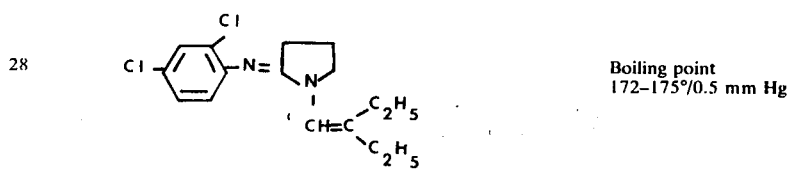 | Boiling point 172–175°/0.5 mm Hg |
| 29 | 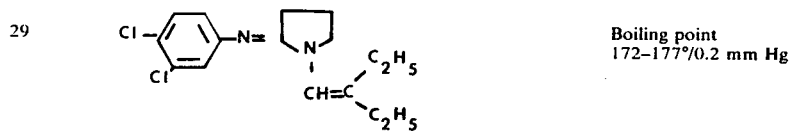 | Boiling point 172–177°/0.2 mm Hg |
| 30 | 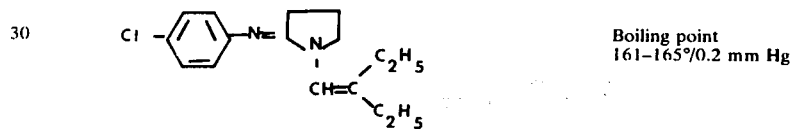 | Boiling point 161–165°/0.2 mm Hg |
| 31 | 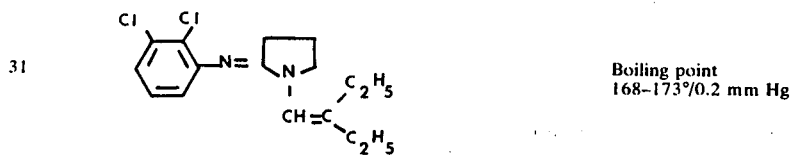 | Boiling point 168–173°/0.2 mm Hg |
| 32 | 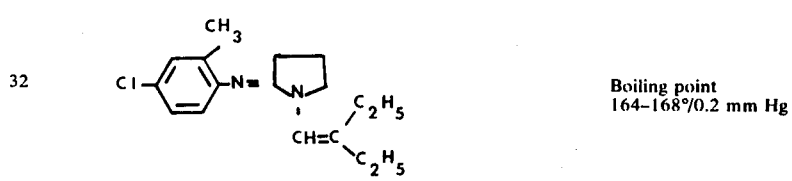 | Boiling point 164–168°/0.2 mm Hg |
| 33 | 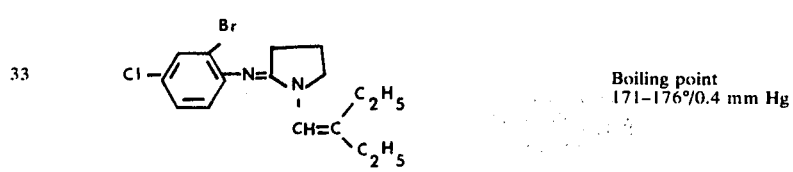 | Boiling point 171–176°/0.4 mm Hg |

| Example No. | Formulae of Examples 2–34 | Physical constants |
|---|---|---|
| 34 | Cl—⟨phenyl(3-CH₃)⟩—N=⟨pyrrolidine ring⟩, N-CH=C(C₂H₅)₂ | Boiling point 173–178°/0.5 mm Hg |

EXAMPLE 35

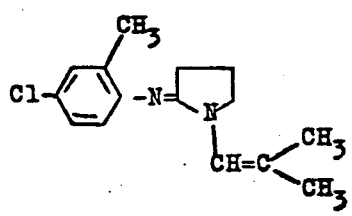

738 g of 2-methyl-4-chloro-aniline hydrochloride (97.8% strength) are introduced into 618 g of N-isobutenyl-pyrrolidone at 15° – 20°C. Thereafter, 660 g of phosphorus oxychloride are added dropwise at 15° – 20°C, with slight cooling. The mixture is then stirred for a further hour at 20°C and is warmed to 80°C in the course of one hour. In the course thereof, a vigorous evolution of hydrogen chloride starts. The mixture is stirred for approximately a further hour at 80° – 85°C, until 2-methyl-4-chloro-aniline is no longer detectable by diazotisation and coupling. The batch is allowed to cool somewhat, and the viscous melt is poured into 30 liters of water at 20° – 25°C, while stirring well. After one hour, all has dissolved apart from small amounts of oily by-products. Active charcoal and filtration aid are added and the acid solution of the reaction product is clarified by filtration. 45% strength sodium hydroxide solution is added dropwise to the filtrate at 20° – 25°C, while stirring well and cooling, until pH 8.5 is reached. The reaction product precipitates in the form of a pale yellowish-coloured crystalline suspension; seeding is used if necessary. After completion of the precipitation, the mixture is stirred for a further 30 minutes at 20° and the crystalline product is filtered off and washed with a large amount of water. After drying in vacuo, the yield is 920 g (86.5 g of theory). Melting point: 68° – 70°C; after recrystallisation from petroleum ether, melting point: 71° – 72°C. The purity of the crude product, determined by gas chromatograhy, is 98 – 99.5%.

EXAMPLE 36

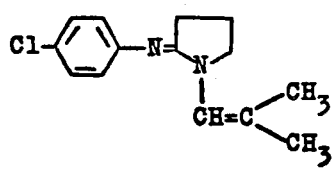

100 g of 4-chloroaniline and 126 g of N-isobutenyl-pyrrolidone are dissolved in 800 ml of benzene and 132 g of phosphorus oxychloride are added dropwise at 20°C, with stirring. Thereafter the mixture is heated to reflux in the course of one hour and is kept refluxing for 1 – 2 hours, until 4-chloroaniline is no longer detectable in a sample by diazotisation and coupling. Thereafter the batch, from which the reaction product has precipitated as a lower oily layer, is poured into 5 liters of ice water and 300 ml of 45% strength sodium hydroxide solution, whilst stirring. The benzene layer is separated off and dried over potassium carbonate, the solvent is distilled off and the reaction product is fractionated in vacuo: boiling point$_{0.3mm}$: 158°–162°C; yield 173 g (81% of theory).

The compounds of Examples 37–39 are analogously produced from the appropriate N-substituted pyrrolidones and arylamines.

| Example No. | Formulae of Examples 37–39 | Physical constants |
|---|---|---|
| 37 | Cl—⟨phenyl⟩—N=⟨pyrrolidine⟩, N-cyclohexenyl | Boiling point 168 to 171°C/0.3 mm Hg |
| 38 | Cl—⟨phenyl⟩—N=⟨pyrrolidine⟩, N-CH=⟨cyclohexenyl⟩ | Boiling point 175 to 179°C/0.1 mm Hg |
| 39 | Cl—⟨phenyl(2-Cl)⟩—N=⟨pyrrolidine⟩, N-CH=⟨cyclohexenyl⟩ | Boiling point 185 to 190°C/0.05 mm Hg |

The compounds of Examples 40–56 are analogously produced from the appropriate N-substituted pyrrolidones and arylamines.

| Example No. | Formulae of Examples 40–56 | Physical constants |
|---|---|---|
| 40 | 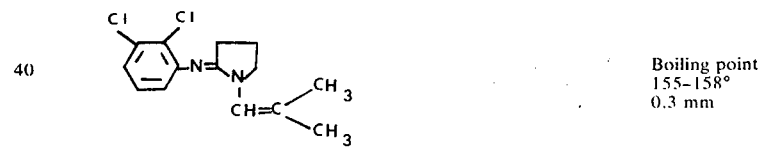 | Boiling point 155–158° 0.3 mm |
| 41 | 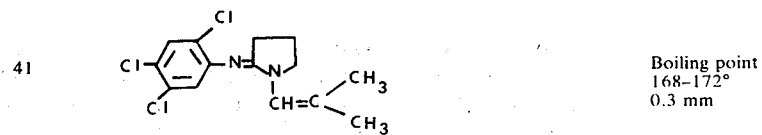 | Boiling point 168–172° 0.3 mm |
| 42 | 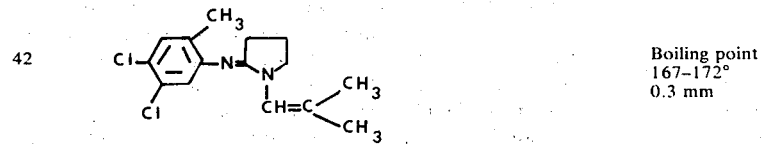 | Boiling point 167–172° 0.3 mm |
| 43 | 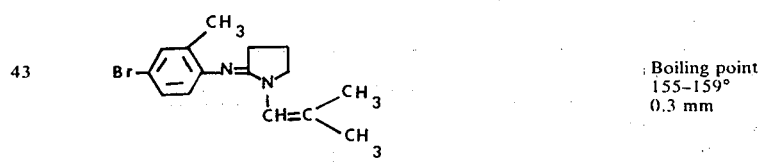 | Boiling point 155–159° 0.3 mm |
| 44 | 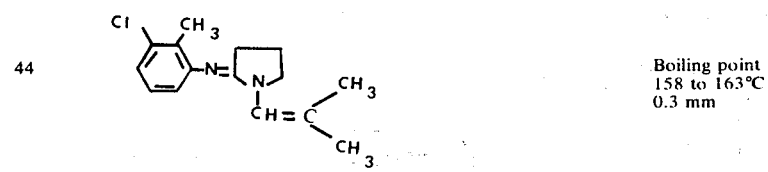 | Boiling point 158 to 163°C 0.3 mm |
| 45 | 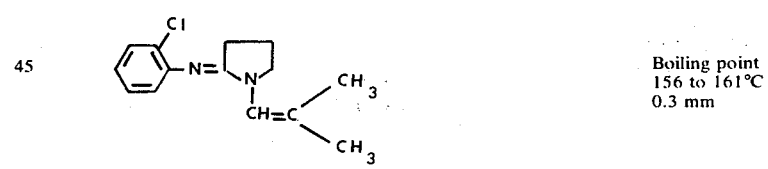 | Boiling point 156 to 161°C 0.3 mm |
| 46 | 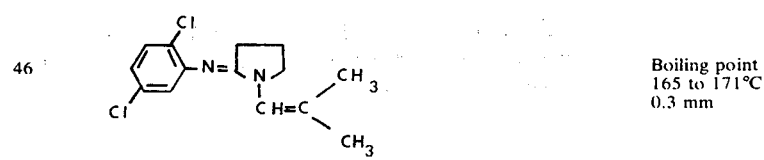 | Boiling point 165 to 171°C 0.3 mm |

-continued

| Example No. | Formulae of Examples 40–56 | Physical constants |
|---|---|---|
| 47 | 2-Cl, 4-CH₃-C₆H₃-N=pyrrolidinylidene, N-CH=C(CH₃)₂ | Boiling point 153 to 156°C 0.3 mm |
| 48 | 2,4,6-trichlorophenyl-N=pyrrolidinylidene, N-CH=C(CH₃)₂ | Boiling point 160 to 164°C 0.3 mm |
| 49 | 4-Cl, 2-CH₃-C₆H₃-N=pyrrolidinylidene, N-CH=CH-CH₂-CH₃ | Boiling point 145 to 147°C 0.2 mm |
| 50 | 4-Cl, 2-Br-C₆H₃-N=pyrrolidinylidene, N-CH=C(CH₃)₂ | Boiling point 172–180°/ 0.5 mm Hg |
| 51 | 2,4-dibromophenyl-N=pyrrolidinylidene, N-CH=C(CH₃)₂ | Boiling point 175–180°/ 0.15 mm Hg |
| 52 | 2,4-dichlorophenyl-N=pyrrolidinylidene, N-CH=C(CH₃)(C₂H₅) | Boiling point 163–166°/ 0.3 mm Hg |
| 53 | 4-Br, 2-Cl-C₆H₃-N=pyrrolidinylidene, N-CH=C(CH₃)(C₂H₅) | Boiling point 165–174°/ 0.2 mm Hg |

| Example No. | Formulae of Examples 40–56 | Physical constants |
|---|---|---|
| 54 | Cl–⟨benzene(Br)⟩–N=⟨pyrrolidine⟩, CH=C(CH$_3$)(C$_2$H$_5$) | Boiling point 162–168°/ 0.2 mm Hg |
| 55 | Cl,Cl,Cl–⟨benzene⟩–N=⟨pyrrolidine⟩, CH=C(CH$_3$)(C$_2$H$_5$) | Boiling point 175–180°/ 0.2 mm Hg |
| 56 | Cl–⟨benzene(CH$_3$)⟩–N=⟨pyrrolidine⟩, CH=C(CH$_3$)(C$_2$H$_5$) | Boiling point 164–169°/ 0.3 mm Hg |

IN VITRO TEST OF OVICIDAL ACTION ON TICKS 3 g of each active substance to be tested are mixed with 7 g of a mixture of equal parts by weight of ethylene glycol monomethyl ether ad nonylphenyl polyglycol ether. The emulsion concentrate thus obtained is diluted with water to the particular desired use concentration.

Adult fully bloated female ticks of the variety Boophilus microplus (resistant) are dipped for one minute into this active substance preparation. After dipping 10 female specimens of each of the various tick strains, the individual ticks are transferred into plastic dishes, the base of which is covered with a disc of filter paper.

After 35 days the activity of each active substance preparation is determined by assessing the inhibition of deposition of fertile eggs, as compared to the deposition of eggs by untreated control ticks. The action is indicated in %: 100% means that no further fertile eggs were deposited and 50% means that the ticks have laid half the number of eggs laid by the untreated control ticks.

Table A sets forth the results from two representative compounds of Belgian patent No. 734,934, while Table B sets forth the results from representative compounds of the present invention.

Table A

| | In vitro test for ovicidal action on ticks | | |
|---|---|---|---|
| Source of active substance | Active substance | Physical constants | Ovicidal action against Boophilus, Biarra strain 100% inhibition / >50% inhibition at the indicated active substance concentration (% by weight) |
| according to Belgian Patent 734,934 | Cl,Cl–⟨benzene⟩–N⟨pyrrolidine⟩–CH$_2$–CH=CH$_2$ (Example 2) | Boiling point 160–164° 0.8 mm | 0.1 / 0.03 |
| | Cl,Cl–⟨benzene⟩–N⟨pyrrolidine(CH$_3$)⟩–CH$_2$–C=CH$_2$ (Example 73) | Boiling point 156–162° 0.2 mm | 0.03 / 0.01 |

Table B

In vitro test for ovicidal action on ticks

| Compounds of the present invention | Active substance | Physical constants | Ovicidal action against Boophilus, Biarra strain 100% inhibition / >50% inhibition at the indicated active substance concentration (% by weight) | |
|---|---|---|---|---|
| Example 1 | 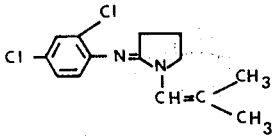 | Melting point: 54.5 °C Boiling point 155–158° 0.2 mm | 0.003 | 0.001 |
| Example 35 | 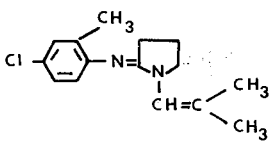 | Melting point: 71–72°C | 0.01 | 0.003 |
| Example 40 | 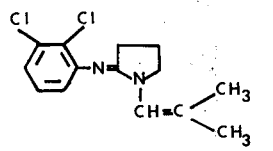 | Boiling point 155–158° 0.3 mm | 0.01 | 0.003 |
| Example 41 | 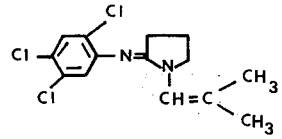 | Boiling point 168–172° 0.3 mm | 0.01 | 0.003 |
| Example 42 | 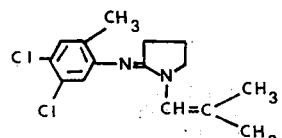 | Boiling point 167–172° 0.3 mm | 0.03 At a concentration of 0.0003% the compound has a 100% lethal effect on tick larvae | 0.01 |
| Example 43 | 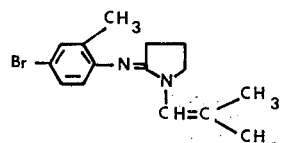 | Boiling point 155–159° 0.3 mm | 0.01 | 0.005 |

Table B-continued

| Compounds of the present invention | Active substance | Physical constants | Ovicidal action against Boophilus, Biarra strain 100% inhibition | >50% inhibition at the indicated active substance concentration (% by weight) |
|---|---|---|---|---|
| Example 44 | 3-Cl, 2-CH₃-C₆H₃-N=pyrrolidinyl-CH=C(CH₃)₂ | Boiling point 158 to 163°C 0.3 mm | 0.01 | 0.005 |
| Example 36 | 4-Cl-C₆H₄-N=pyrrolidinyl-CH=C(CH₃)₂ | Boiling point 158 to 162°C 0.3 mm | 0.03 | 0.02 |
| Example 45 | 2-Cl-C₆H₄-N=pyrrolidinyl-CH=C(CH₃)₂ | Boiling point 156 to 161°C 0.3 mm | 0.03 | 0.02 |
| Example 46 | 2,5-diCl-C₆H₃-N=pyrrolidinyl-CH=C(CH₃)₂ | Boiling point 165 to 171°C 0.3 mm | 0.03 | 0.01 |
| Example 47 | 2-Cl, 4-CH₃-C₆H₃-N=pyrrolidinyl-CH=C(CH₃)₂ | Boiling point 153 to 156°C 0.3 mm | 0.03 | 0.02 |
| Example 48 | 2,6-diCl-C₆H₃-N=pyrrolidinyl-CH=C(CH₃)₂ | Boiling point 160 to 164°C 0.3 mm | 0.03 | 0.02 |

Table B-continued

In vitro test for ovicidal action on ticks

| Compounds of the present invention | Active substance | Physical constants | Ovicidal action against Boophilus, Biarra strain 100% inhibition / >50% inhibition at the indicated active substance concentration (% by weight) | |
|---|---|---|---|---|
| Example 49 | Cl-C₆H₃(CH₃)-N=C(pyrrolidine)-CH=CH-CH₂-CH₃ | Boiling point 145 to 147°C 0.2 mm | 0.003 | 0.002 |
| Example 50 | Cl-C₆H₃(Br)-N=C(pyrrolidine)-CH=C(CH₃)₂ | Boiling point 172–180°/ 0.5 mm Hg | 0.01 | 0.005 |
| Example 51 | Br-C₆H₃(Br)-N=C(pyrrolidine)-CH=C(CH₃)₂ | Boiling point 175–180°/ 0.15 mm Hg | 0.01 | 0.003 |
| Example 52 | Cl-C₆H₃(Cl)-N=C(pyrrolidine)-CH=C(CH₃)(C₂H₅) | Boiling point 163–166°/ 0.3 mm Hg | 0.01 | 0.003 |
| Example 53 | Br-C₆H₃(Cl)-N=C(pyrrolidine)-CH=C(CH₃)(C₂H₅) | Boiling point 165–174°/ 0.2 mm Hg | 0.03 | 0.01 |
| Example 54 | Cl-C₆H₃(Br)-N=C(pyrrolidine)-CH=C(CH₃)(C₂H₅) | Boiling point 162–168°/ 0.2 mm Hg | 0.03 | 0.01 |

Table B-continued

| Compounds of the present invention | In vitro test for ovicidal action on ticks | | Ovicidal action against Boophilus, Biarra strain | |
|---|---|---|---|---|
| | Active substance | Physical constants | 100% inhibition | >50% inhibition |
| | | | at the indicated active substance concentration (% by weight) | |
| Example 55 | Cl-phenyl(Cl,Cl)-N=pyrrolidine with CH=C(CH₃)(C₂H₅) | Boiling point 175–180°/ 0.2 mm Hg | 0.03 | 0.01 |
| Example 56 | Cl-phenyl(CH₃)-N=pyrrolidine with CH=C(CH₃)(C₂H₅) | Boiling point 164–169°/ 0.3 mm Hg | 0.01 | 0.003 |

What is claimed is:

1. A pharmaceutical composition useful for treating tick infestation in animals which comprises an effective amount of a compound of the formula

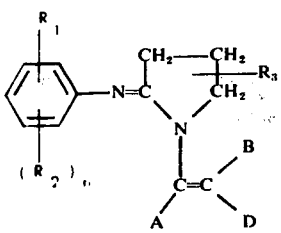

or a salt thereof, wherein
R₁ is halogen,
R₂ is hydrogen, halogen, alkyl of 1 to 6 carbon atoms, difluoromethyl or trifluoromethyl,
R₃ is hydrogen or lower alkyl,
n is an integer from 1 to 4, and
A, B and D each represent hydrogen, alkyl of 1 to 6 carbon atoms, alkenyl of 2 to 6 carbon atoms, or A and B, or B and D, are linked to each other to form a ring, provided that at least one of A, B and D is alkyl or alkenyl,
in combination with a solid or liquified gaseous carrier, or in combination with a carrier containing a surface-active agent.

2. A composition according to claim 1, wherein R₁ is chlorine, bromine or fluorine, R₂ is hydrogen, chlorine, bromine, fluorine, methyl, ethyl, difluoromethyl or trifluoromethyl, and R₃ is hydrogen or alkyl of 1 to 4 carbon atoms.

3. A composition according to claim 1 wherein
R₁ is chlorine or bromine,
R₂ is hydrogen, chlorine, bromine, methyl, ethyl or trifluoromethyl,
R₃ is hydrogen,
n is 1 or 2, and
A, B and D each represent hydrogen, methyl or ethyl, or A and B, or B and D are alkyl or alkenyl linked to each other to form a 6-membered ring, provided that, at least one of A, B and D is alkyl or alkenyl.

4. The composition according to claim 1 wherein the compound is

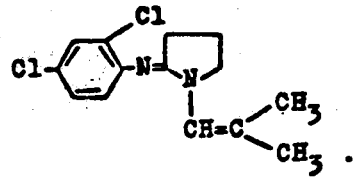

5. The composition according to claim 1 wherein the compound is

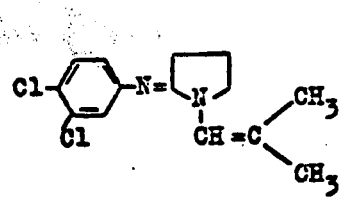

6. The composition according to claim 1 wherein the compound is

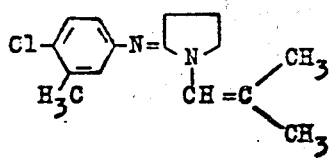

7. The composition according to claim 1 wherein the compound is

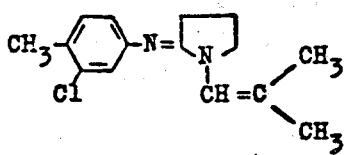

8. The composition according to claim 1 wherein the compound is

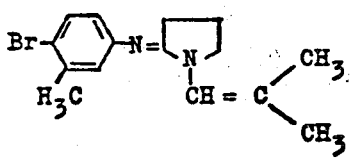

9. The composition according to claim 1 wherein the compound is

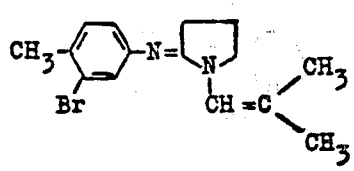

10. The composition according to claim 1 wherein the compound is

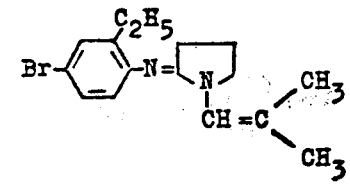

11. The composition according to claim 1 wherein the compound is

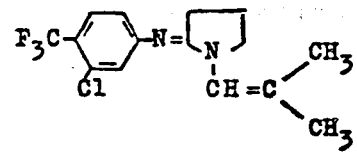

12. The composition according to claim 1 wherein the compound is

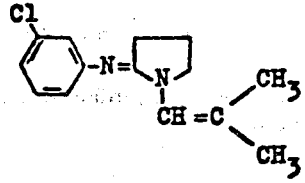

13. The composition according to claim 1 wherein the compound is

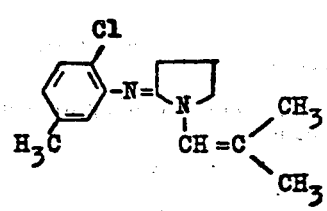

14. The composition according to claim 1 wherein the compound is

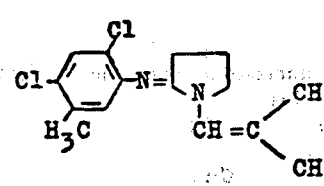

15. The composition according to claim 1 wherein the compound is

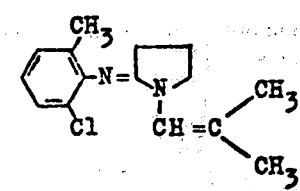

16. The composition according to claim 1 wherein the compound is

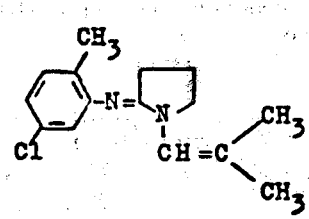

17. The composition according to claim 1 wherein the compound is

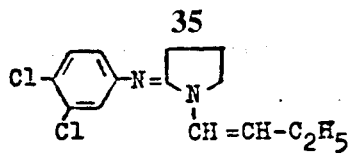

18. The composition according to claim 1 wherein the compound is

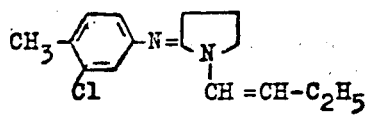

19. The composition according to claim 1 wherein the compound is

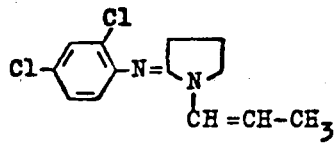

20. The composition according to claim 1 wherein the compound is

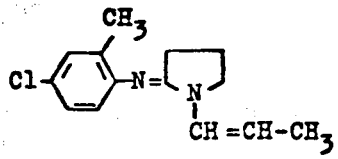

21. The composition according to claim 1 wherein the compound is

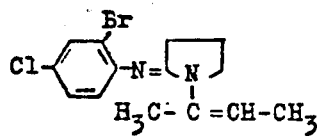

22. The composition according to claim 1 wherein the compound is

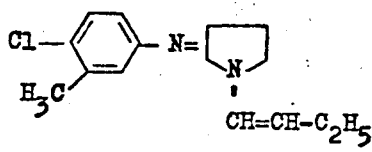

23. The composition according to claim 1 wherein the compound is

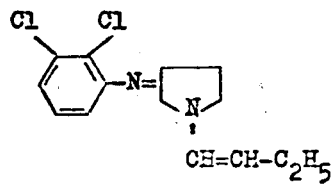

24. The composition according to claim 1 wherein the compound is

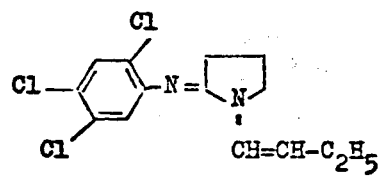

25. The composition according to claim 1 wherein the compound is

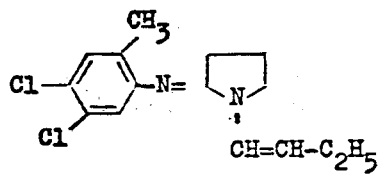

26. The composition according to claim 1 wherein the compound is

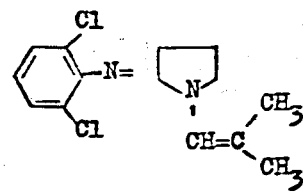

27. The composition according to claim 1 wherein the compound is

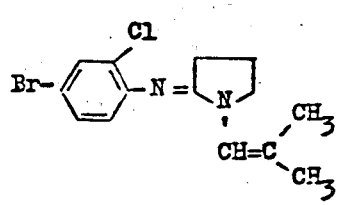

28. The composition according to claim 1 wherein the compound is

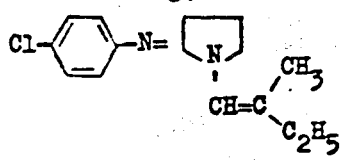

29. The composition according to claim 1 wherein the compound is

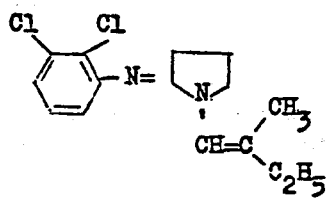

30. The composition according to claim 1 wherein the compound is

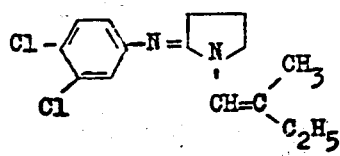

31. The composition according to claim 1 wherein the compound is

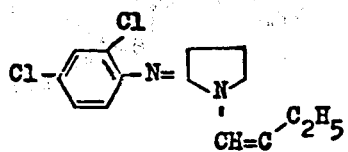

32. The composition according to claim 1 wherein the compound is

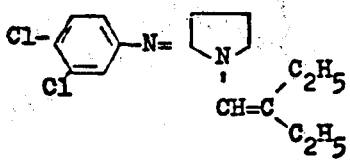

33. The composition according to claim 1 wherein the compound is

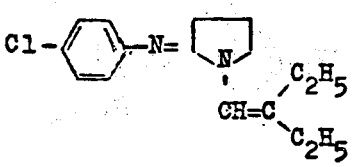

34. The composition according to claim 1 wherein the compound is

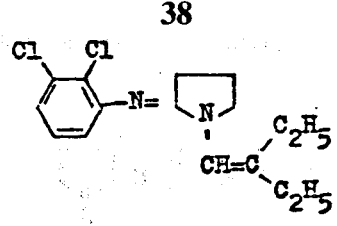

35. The composition according to claim 1 wherein the compound is

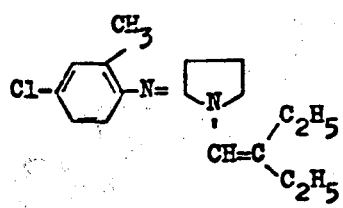

36. The composition according to claim 1 wherein the compound is

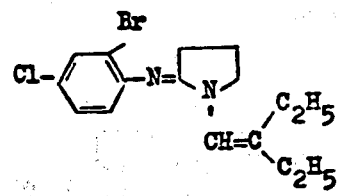

37. The composition according to claim 1 wherein the compound is

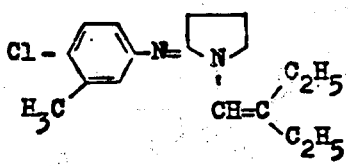

38. The composition according to claim 1 wherein the compound is

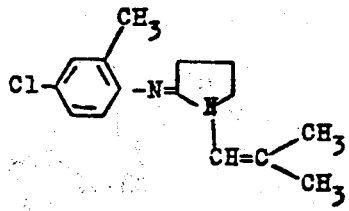

39. The composition according to claim 1 wherein the compound is

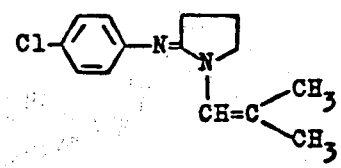

40. The composition according to claim 1 wherein the compound is

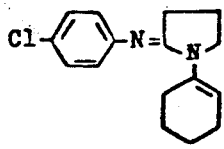

41. The composition according to claim 1 wherein the compound is

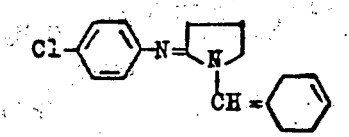

42. The composition according to claim 1 wherein the compound is

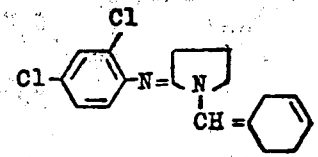

43. The composition according to claim 1 wherein the compound is

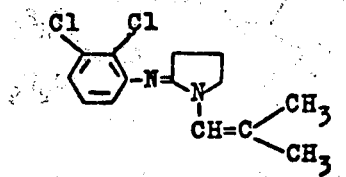

44. The composition according to claim 1 wherein the compound is

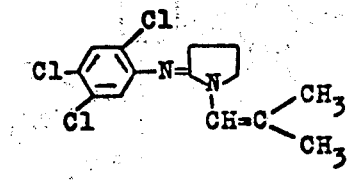

45. The composition according to claim 1 wherein the compound is

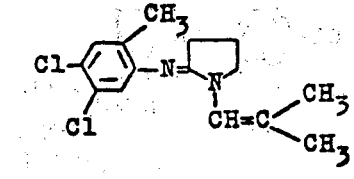

46. The composition according to claim 1 wherein the compound is

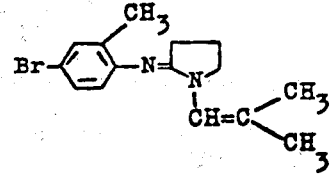

47. The composition according to claim 1 wherein the compound is

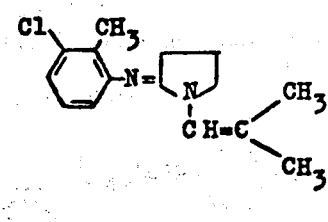

48. The composition according to claim 1 wherein the compound is

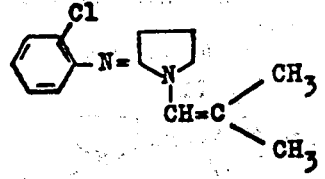

49. The composition according to claim 1 wherein the compound is

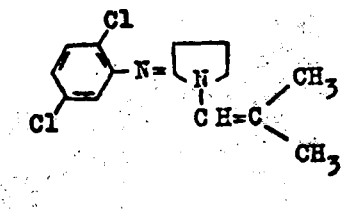

50. The composition according to claim 1 wherein the compound is

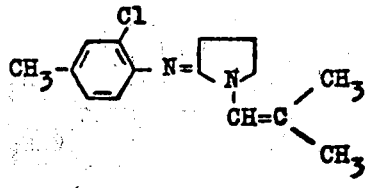

51. The composition according to claim 1 wherein the compound is

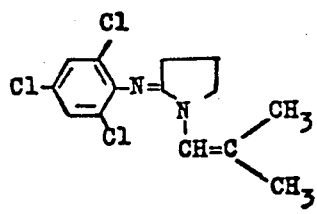

52. The composition according to claim 1 wherein the compound is

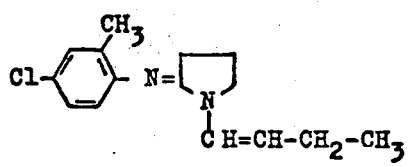

53. The composition according to claim 1 wherein the compound is

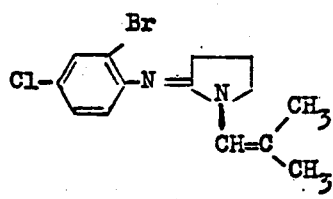

54. The composition according to claim 1 wherein the compound is

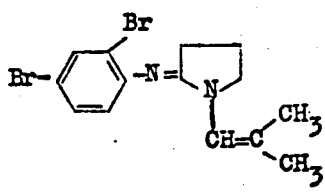

55. The composition according to claim 1 wherein the compound is

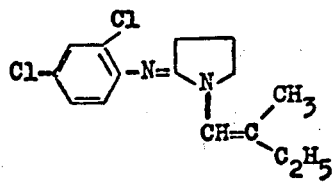

56. The composition according to claim 1 wherein the compound is

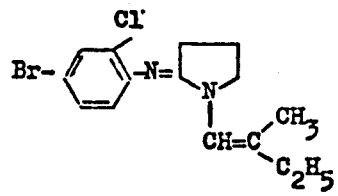

57. The composition according to claim 1 wherein the compound is

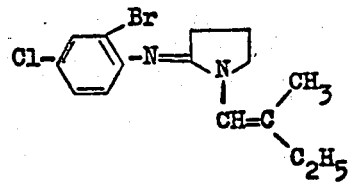

58. The composition according to claim 1 wherein the compound is

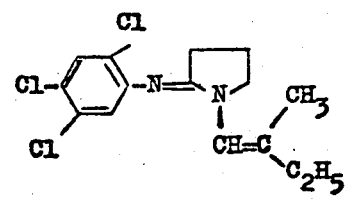

59. The composition according to claim 1 wherein the compound is

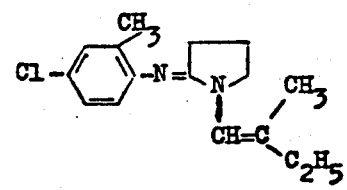

60. A composition according to claim 1 which contains 0.1 to 95 per cent by weight of active compound.

61. A composition according to claim 1 in solution form.

62. A composition according to claim 1 in the form of an emulsion.

63. A composition according to claim 1 in the form of a suspension.

64. A composition according to claim 1 in powder form.

65. A composition according to claim 1 in paste form.

66. A composition according to claim 1 in granulate form.

67. A method of protecting or freeing animals from ticks and of combating ticks in animals which comprises applying externally to such animal or to the tick or to its habitat and effective amount of a compound of the formula

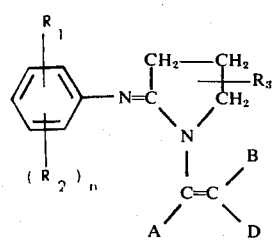

or a salt thereof, wherein
R₁ is halogen,
R₂ is hydrogen, halogen, alkyl of 1 to 6 carbon atoms difluoromethyl or trifluoromethyl,
R₃ is hydrogen or lower alkyl,
n is an integer from 1 to 4, and
A, B and D each represent hydrogen, alkyl of 1 to 6 carbon atoms, alkenyl of 2 to 6 carbon atoms, or A and B, or B and D, are linked to each other to form a ring, provided that at least one of A, B and D is alkyl or alkenyl.

68. A method of combating ticks which comprises applying to the tick or to their habitat an effective amount of a composition according to claim 1, which composition contains 10 to 50,000 ppm of active compound.

69. A method according to claim 67 wherein
R₁ is chlorine, bromine or fluorine,
R₂ is hydrogen, chlorine, bromine, fluorine, methyl, ethyl, difluoromethyl or trifluoromethyl, and
R₃ is hydrogen or alkyl of 1 to 4 carbon atoms.

70. A method according to claim 67
wherein
R₁ is chlorine or bromine,
R₂ is hydrogen, chlorine, bromine, methyl, ethyl or trifluoromethyl,
R₃ is hydrogen,
n is 1 or 2 and
A, B and D each represent hydrogen, methyl or ethyl, or A and B, or B and D are alkyl or alkenyl linked to each other to form a 6-membered ring, provided that at least one of A, B and D is alkyl or alkenyl.

71. A method according to claim 67 wherein the active compound is

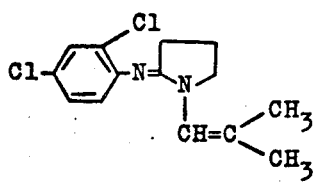

72. A method according to claim 67 wherein the active compound is

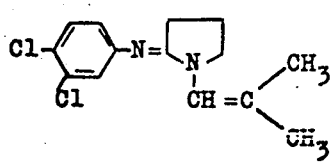

73. A method according to claim 67 wherein the active compound is

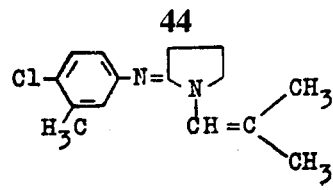

74. A method according to claim 67 wherein the active compound is

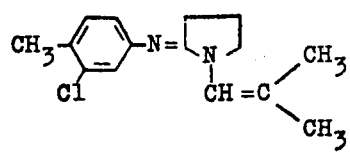

75. A method according to claim 67 wherein the active compound is

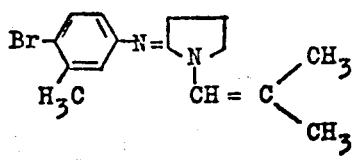

76. A method according to claim 67 wherein the active compound is

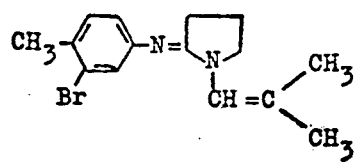

77. A method according to claim 67 wherein the active compound is

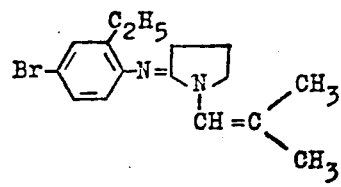

78. A method according to claim 67 wherein the active compound is

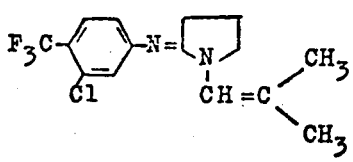

79. A method according to claim 67 wherein the active compound is

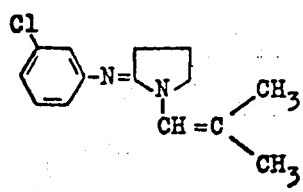

80. A method according to claim 67 wherein the active compound is

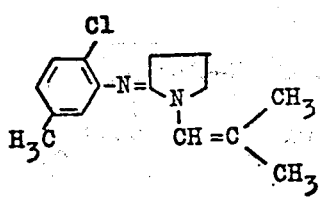

81. A method according to claim 67 wherein the active compound is

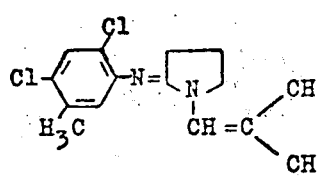

82. A method according to claim 67 wherein the active compound is

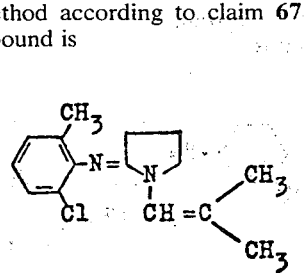

83. A method according to claim 67 wherein the active compound is

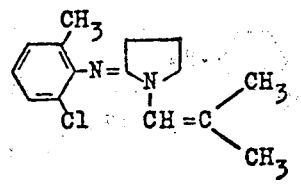

84. A method according to claim 67 wherein the active compound is

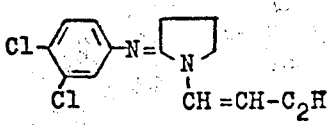

85. A method according to claim 67 wherein the active compound is

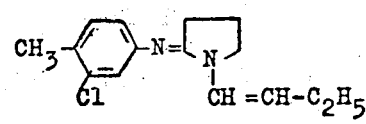

86. A method according to claim 67 wherein the active compound is

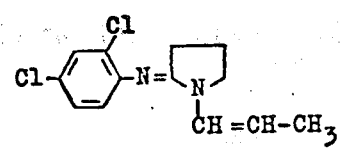

87. A method according to claim 67 wherein the active compound is

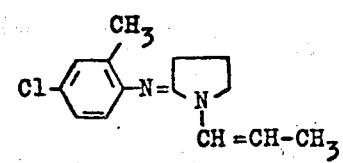

88. A method according to claim 67 wherein the active compound is

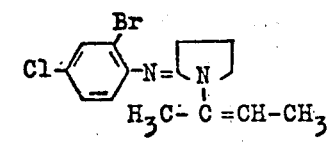

89. A method according to claim 67 wherein the active compound is

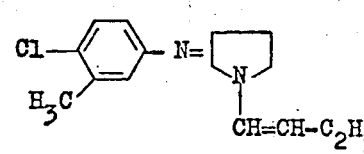

90. A method according to claim 67 wherein the active compound is

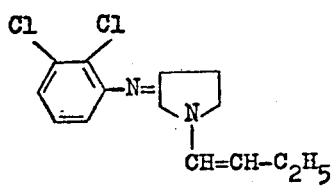

91. A method according to claim 67 wherein the active compound is

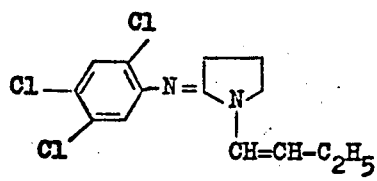

92. A method according to claim 67 wherein the active compound is

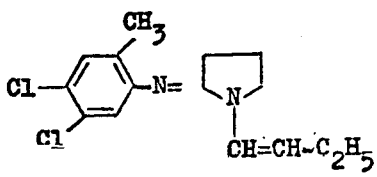

93. A method according to claim 67 wherein the active compound is

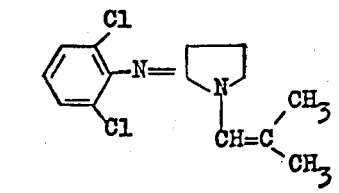

94. A method according to claim 67 wherein the active compound is

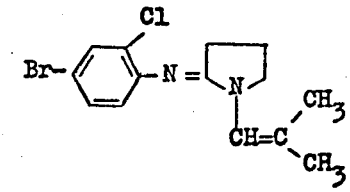

95. A method according to claim 67 wherein the active compound is

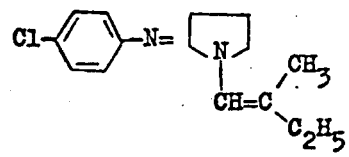

96. A method according to claim 67 wherein the active compound is

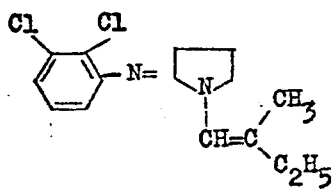

97. A method according to claim 67 wherein the active compound is

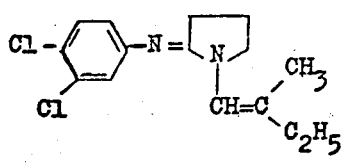

98. A method according to claim 67 wherein the active compound is

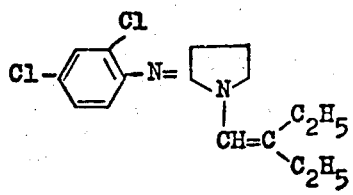

99. A method according to claim 67 wherein the active compound is

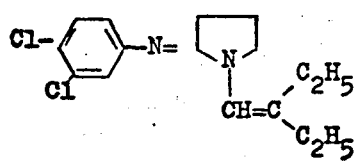

100. A method according to claim 67 wherein the active compound is

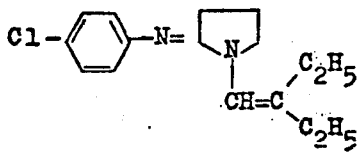

101. A method according to claim 67 wherein the active compound is

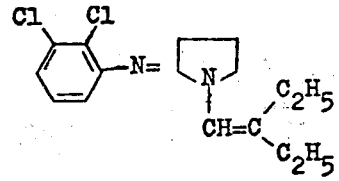

102. A method according to claim 67 wherein the active compound is

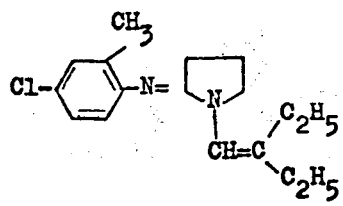

103. A method according to claim 67 wherein the active compound is

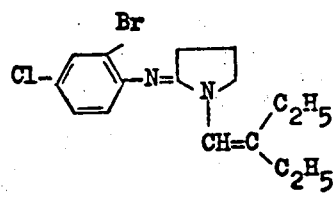

104. A method according to claim 67 wherein the active compound is

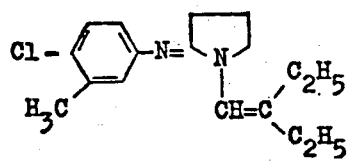

105. A method according to claim 67 wherein the active compound is

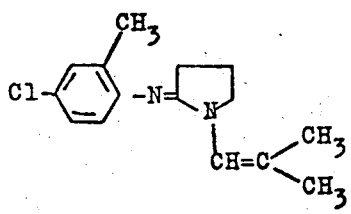

106. A method according to claim 67 wherein the active compound is

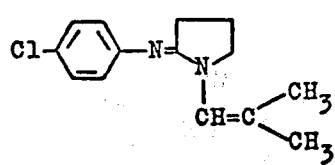

107. A method according to claim 67 wherein the active compound is

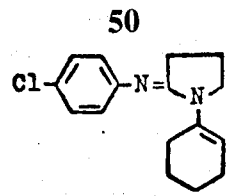

108. A method according to claim 67 wherein the active compound is

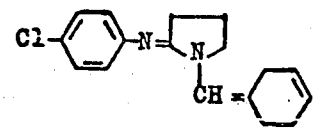

109. A method according to claim 67 wherein the active compound is

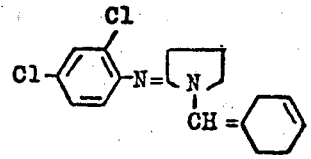

110. A method according to claim 67 wherein the active compound is

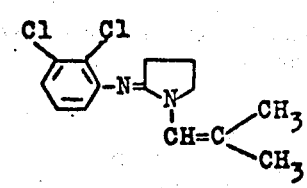

111. A method according to claim 67 wherein the active compound is

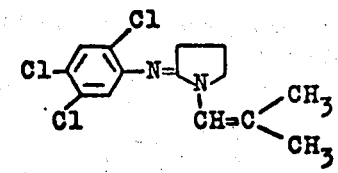

112. A method according to claim 67 wherein the active compound is

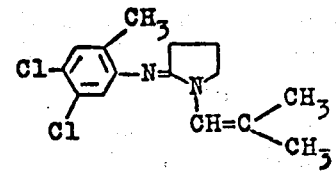

113. A method according to claim 67 wherein the active compound is

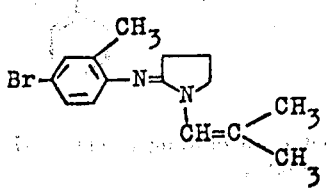

114. A method according to claim 67 wherein the active compound is

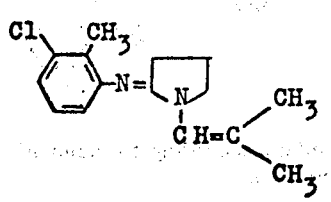

115. A method according to claim 67 wherein the active compound is

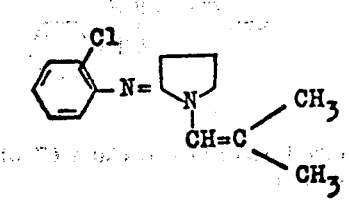

116. A method according to claim 67 wherein the active compound is

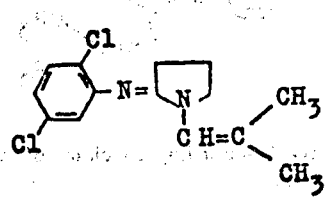

117. A method according to claim 67 wherein the active compound is

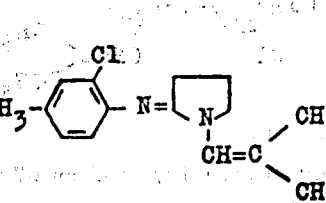

118. A method according to claim 67 wherein the active compound is

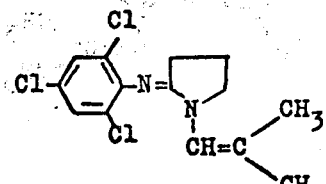

119. A method according to claim 67 wherein the active compound is

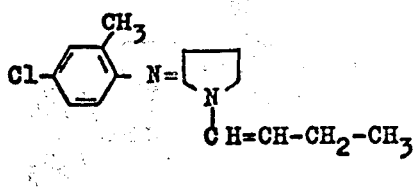

120. A method according to claim 67 wherein the active compound is

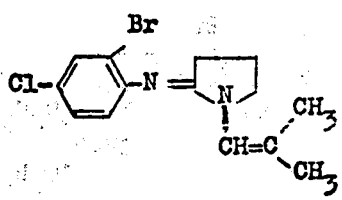

121. A method according to claim 67 wherein the active compound is

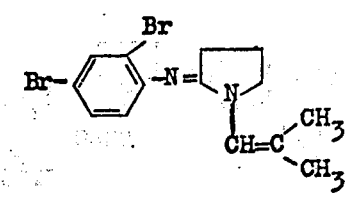

122. A method according to claim 67 wherein the active compound is

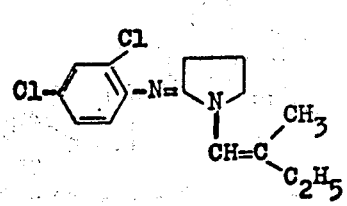

123. A method according to claim 67 wherein the active compound is

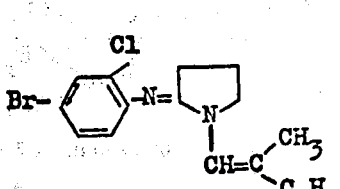

124. A method according to claim 67 wherein the active compound is

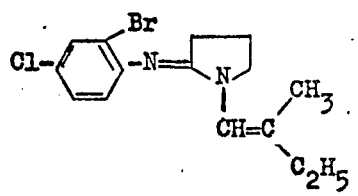

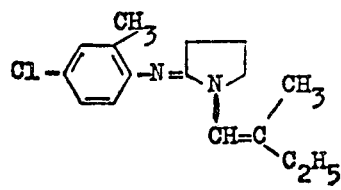

125. A method according to claim 67 wherein the active compound is

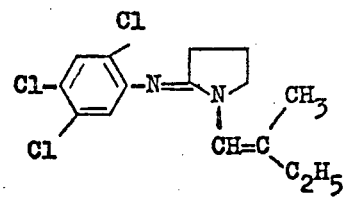

126. A method according to claim 67 wherein the active compound is

127. A method according to claim 68 wherein the composition is in solution form.

128. A method according to claim 68 wherein the composition is in the form of an emulsion.

129. A method according to claim 68 wherein the composition is in the form of a suspension.

130. A method according to claim 68 wherein the composition is in powder form.

131. A method according to claim 68 wherein the composition is in paste form.

132. A method according to claim 68 wherein the composition is in granulate form.

* * * * *